(12) United States Patent
Bakker et al.

(10) Patent No.: US 7,094,779 B2
(45) Date of Patent: Aug. 22, 2006

(54) PIPERAZINE OXIME DERVATIVES HAVING NK-1 RECEPTOR ANTAGONISTIC ACTIVITY

(75) Inventors: Wouter I. Iwema Bakker, Weesp (NL); Jan H. van Maarseveen, Weesp (NL); Hein K. A. C. Coolen, Weesp (NL); Martinus Th. M. Tulp, Weesp (NL); Arnoldus H. J. Herremans, Weesp (NL); Andrew C. Mccreary, Weesp (NL); Gustaaf J. M. van Scharrenburg, Weesp (NL); Adrianus van den Hoogenband, Weesp (NL)

(73) Assignee: Solvay Pharmaceuticals B.V., Weesp (NL)

( * ) Notice: Subject to any disclaimer, the term of this patent is extended or adjusted under 35 U.S.C. 154(b) by 63 days.

(21) Appl. No.: 10/480,542

(22) PCT Filed: Jul. 3, 2002

(86) PCT No.: PCT/EP02/07472

§ 371 (c)(1),
(2), (4) Date: Dec. 12, 2003

(87) PCT Pub. No.: WO03/006459

PCT Pub. Date: Jan. 23, 2003

(65) Prior Publication Data

US 2004/0176389 A1    Sep. 9, 2004

(30) Foreign Application Priority Data

Jul. 9, 2001    (EP)    .................................. 01202631

(51) Int. Cl.
*A61K 31/496* (2006.01)
*C07D 403/06* (2006.01)
*C07D 413/14* (2006.01)
*C07D 471/04* (2006.01)

(52) U.S. Cl. .............................. 514/228.2; 514/233.5; 514/252.11; 514/252.13; 514/253.04; 514/253.09; 514/254.06; 514/254.09; 514/255.01; 544/61; 544/121; 544/357; 544/362; 544/364; 544/371; 544/373; 544/389; 544/391; 544/403; 544/376

(58) Field of Classification Search ................ 544/373, 544/364, 61, 121, 362, 371, 357, 376, 391, 544/389, 403; 514/253.09, 254.09, 228.2, 514/233.5, 252.11, 253.04, 254.06, 252.13, 514/255.01
See application file for complete search history.

(56) References Cited

U.S. PATENT DOCUMENTS 6,001,833 A    12/1999   Jasserand et al.

FOREIGN PATENT DOCUMENTS

| EP | 0 655 442 A1 | 5/1995 |
|---|---|---|
| EP | 0 832 887 A1 | 4/1998 |
| EP | 0 899 270 A1 | 3/1999 |
| WO | WO 96/34857 | 11/1996 |
| WO | WO 96/34864 | 11/1996 |
| WO | WO 96/37489 | 11/1996 |
| WO | WO 97/22597 | 6/1997 |
| WO | WO 98/57954 | 12/1998 |
| WO | WO 00/39114 | 7/2000 |

OTHER PUBLICATIONS

Herrin et al. J.Med. Chem. vol. 18, p. 1216-1223 (1975).*

* cited by examiner

*Primary Examiner*—Emily Bernhardt
(74) *Attorney, Agent, or Firm*—Finnegan, Henderson, Farabow, Garrett & Dunner, L.L.P.

(57) ABSTRACT

The present invention relates to a group of novel piperazine oxime derivatives having interesting NK-1 antagonistic activity. The invention relates to compounds of the general formula (1) wherein: X represents phenyl or pyridyl substituted with 1 or 2 substituents from the group $CH_3$, $CF_3$, $OCH_3$, halogen, cyano and 5-$CF_3$-tetrazol-1-yl; Y represents 2- or 3-indolyl, phenyl, 7-aza-indol-3-yl or 3-indazolyl, 2-naphthyl, 3-benzo[b]thiophenyl, 2-benzofuranyl, which groups may be substituted with one or more halogen or alkyl (1–3C); n has the value 0–3; m has the value 0–2; $R_1$ represents $NH_2$, NH-alkyl (1–3C), dialkyl (1–3C)N, morpholino or morpholino substituted with one or two methyl and/or methoxymethyl groups, thiomorpholino, 1,1-dioxothiomorpholino, 2-, 3- or 4-pyridyl or 4-$CH_3$-piperazinyl; $R_2$ is hydrogen, alkyl (1–4C) or phenyl, or $R_2$ together with $(CH_2)_m$ wherein m is 1, and the intermediate carbon, nitrogen and oxygen atoms forms an isoxazolyl or a 4,5-dihydroisoxazolyl group; $R_3$ and $R_4$ independently represent hydrogen or methyl, or $R_3$ and $R_4$ together are oxygen. The invention also relates to a method for the preparation of the novel compounds, and to pharmaceutical compositions comprising compounds with formula (1) as an active ingredient and the use of these compounds for the treatment of disorders in which neurokinin-1 receptors are involved (1)

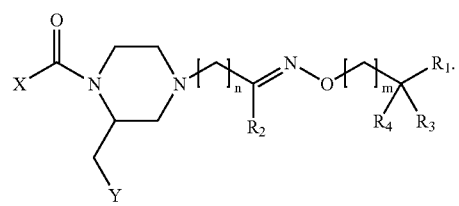

7 Claims, No Drawings

PIPERAZINE OXIME DERVATIVES HAVING NK-1 RECEPTOR ANTAGONISTIC ACTIVITY

The present invention relates to a group of novel piperazine oxime derivatives having interesting NK-1 antagonistic activity.

The invention also relates to a method for the preparation of the novel compounds, and to pharmaceutical compositions comprising at least one of the novel compounds as an active ingredient, and the use of these compositions for the treatment of disorders in which neurokinin-1 receptors are involved.

EP 0899270 relates to 2-(3-indolylmethyl)-1-benzoyl4-[(-2-benzylamino)ethyl) aminocarbonyl)]piperazine derivatives having NK-1 antagonistic activity.

It has now been found that compounds wherein the [(benzylamino)ethyl aminocarbonyl] group at N-4 is replaced by an oxime group also have very interesting NK-1 antagonistic properties.

The invention relates to compounds of the general formula (1)

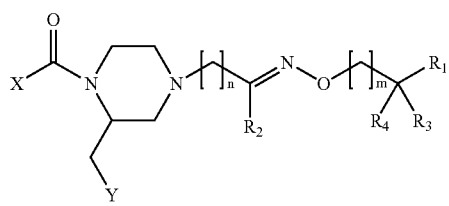

(1)

wherein:
- X represents phenyl or pyridyl substituted with 1 or 2 substituents from the group $CH_3$, $CF_3$, $OCH_3$, halogen, cyano and 5-$CF_3$-tetrazol-1-yl
- Y represents 2- or 3-indolyl, phenyl, 7-aza-indol-3-yl or 3-indazolyl, 2-naphthyl, 3-benzo[b]thiophenyl or 2-benzofuranyl, which groups may be substituted with one or more halogen or alkyl (1–3C)
- n has the value 0–3
- m has the value 0–2
- $R_1$ represents $NH_2$, NH-alkyl (1–3C), dialkyl (1–3C)N, morpholino or morpholino substituted with one or two methyl and/or methoxymethyl groups, thiomorpholino, 1,1-dioxothiomorpholino, 2-, 3- or 4-pyridyl or 4-$CH_3$-piperazinyl
- $R_2$ is hydrogen, alkyl (1–4C) or phenyl, or $R_2$ together with $(CH_2)_m$ wherein m is 1, and the intermediate carbon, nitrogen and oxygen atoms forms an isoxazolyl or a 4,5-dihydroisoxazolyl group,
- $R_3$ and $R_4$ independently represent hydrogen or methyl, or $R_3$ and $R_4$ together are oxygen.

and physiologically acceptable salts thereof.

In the description of the substituents the abbreviation 'alkyl(1–3C)' means: 'methyl, ethyl, n-propyl or isopropyl', and the abbreviation 'alkyl(1–4C)' means 'methyl, ethyl, n-propyl, isopropyl, 1-butyl, 2-butyl, 1-(2-methyl)-propyl and 2-(2-methyl)-propyl'.

The invention particularly relates to compounds having formula (1) wherein Y represents 2- or 3-indolyl, phenyl, 7-aza-indol-3-yl or 3-indazolyl, which groups may be substituted with halogen or alkyl (1–3C); $R_1$ represents $NH_2$, NH-alkyl (1–3C), dialkyl (1–3C)N, morpholino or morpholino substituted with one or two methyl and/or methoxymethyl groups, thiomorpholino, 2-, 3- or 4-pyridyl or 4-$CH_3$-piperazinyl, and $R_3$ and $R_4$ are hydrogen and X, n, m and $R_2$ have the meanings given above.

More particularly the invention relates to compounds having formula (1) wherein X represents phenyl substituted with 2 substituents from the group CF3 and halogen, Y is 3-indolyl, m is 1 or 2, n is 1 or 2 and $R_1$, $R_2$, $R_3$, and $R_4$ have the meanings given above.

Still more particularly the invention relates to such compounds having formula (1) wherein X represents phenyl substituted at positions 3 and 5 with $CF_3$ or halogen.

In this preferred group of compounds having formula (1) m and n have the value 1 or 2, $R_1$ is amino, dimethylamino or morpholino, $R_2$ is hydrogen, methyl or phenyl, or $R_2$ together with $(CH_2)_m$, wherein m=1, and the intermediate carbon, nitrogen and oxygen atoms forms the isoxazolyl group or dihydroisoxazolyl group.

Both compounds having formula (1) wherein the group —$CH_2$—Y has the R-configuration or the S-configuration, and the E- and Z-enantiomers of the oxime-ether belong to the invention.

The compounds having formula (1) and their salts can be obtained according to at least one of the following methods known for compounds of this type.

Compound having formula (1) wherein n has the value 1–3 can be obtained by reaction of a compound having formula (2)

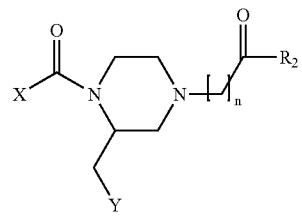

(2)

with a compound of the formula (3)

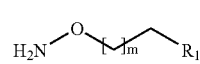

(3)

Wherein X, Y, m, $R_1$ and $R_2$ have the above meanings. This reaction is preferably carried out in a solvent such as methanol or ethanol in the presence of sodium acetate.

Compounds having formula (1) wherein n=0 can be obtained by reaction of a compound having formula (4)

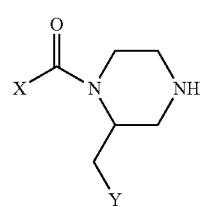

(4)

with, N,N-dimethylformamide dimethylacetal, preferably in acetonitrile at reflux temperature, followed by reaction with a compound having formula (3) for example in THF at reflux temperature.

Compounds having formula (1) wherein n=1, $R_2$ is hydrogen, and $R_1$ is morpholino can be obtained by reaction of a compound having formula (2) with a compound having formula (7)

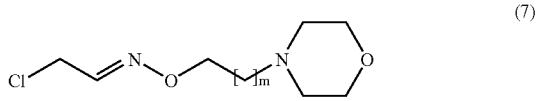

(7)

This reaction can be carried out in a solvent such as acetonitrile in the presence of a base such as triethylamine and KI at temperatures between room temperature and 80° C.

Compounds having formula (1) wherein $R_2$ together with $(CH_2)_m$ and the intermediate atoms forms the isoxazolyl or 4,5-dihydroisoxazolyl group can be obtained by reaction of a compound having formula (4) with a compound having formula (9)

(9)

wherein L is a so-called leaving group, for example chloro or bromo, and the dotted line is a bond or is absent.

The starting materials having formula (2) can be obtained
a) by reaction of a compound having formula (4) with a compound having formula (5)

(5)

wherein L is so-called leaving group, for example chloro or bromo. This reaction is carried out in a solvent such as acetonitrile in the presence of a base such as triethylamine and KI at temperatures between room temperature and 80° C.; or
b) by acidic hydrolysis of a compound obtained from the reaction between a compound having formula (4) with a compound having formula (6)

(6)

wherein the symbols have the above meanings.
The alkylation reaction can be carried out in a solvent such as acetonitrile or dimethylformamide in the presence of a base such as triethylamine and KI at temperatures between room temperature and 80° C. The hydrolysis reaction of the obtained product can be carried out in a solvent such as 1,4-dioxane with 6M HCl (aq.), or
c) by reaction of a compound having formula (4) with methyl vinyl ketone. This reaction is preferably carried out in a solvent such as a toluene at room temperature.

The starting compounds having formula (3) can be prepared
a) by reaction of a compound having formula (8)

(8)

with 1-phenyl ethanone-oxime, followed by acidic hydrolysis, in which formula L is a so-called leaving group, for example bromo or chloro.

The alkylation reaction can be carried out in a biphasic system consisting of a solvent such as toluene and aqueous NaOH and tetrabutylammonium bromide, at a temperature of about 90° C. The hydrolysis can be carried out in 6 M HCl (aq.); or
b) according to the method described by Henmi et al. (Org. Prep. Proceed. Int. 1994, 26, 111).

The starting compounds having formula (4) can be obtained from compounds having formula (10) in a similar manner as described in EP 065542

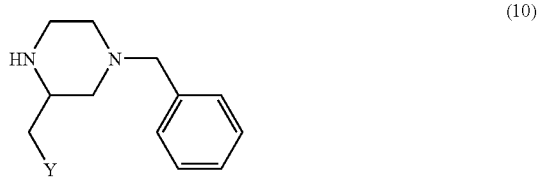

(10)

The starting compounds having formula (7) can be obtained analogous to the synthesis of 1-chloro-2-methoxy-iminoethane as described in *J. Chem. Soc. Perkin Trans.* 1, 1991, 1721.

Starting compounds having formula (9) can be obtained from 2-nitroethyl -2-tetrahydropyranyl ether and the appropriate allyl- or propargylamine, analogous to the method described in *J. Med. Chem.* 1995, 38, 4198.

Starting compounds having formula (10) can be obtained in a similar manner as described in EP 0655442, or from 4-benzyl-piperazine-1-carboxylic acid tert-butyl-ester by alkylation followed by acid treatment.

The alkylation of 4-benzyl-piperazine-1-carboxylic acid tert-butyl ester (T. R. Herrin, J. M. Pauvlik, E. V. Schuber, A. O. Geiszler *J. Med. Chem.* 1975, 18, 1216)can be done in diethylether by anion formation with a strong base, such as sec-butyl lithium in the presence of tetramethylethylene-diamine, at low temperature followed by the addition of a suitable alkylating agent of formula (11).

 YCH$_2$Br (11)

Removal of the tert-butyloxycarbonyl-group can be done using known procedures (T. W. Greene, P. G. M. Wuts *Protective groups in organic synthesis*, 3$^{rd}$ ed., John Wiley & Sons, 1999).

Suitable acid addition salts can be formed with inorganic acids such as hydrochloric acid, sulphuric acid, phosphoric acid and nitric acid, or with organic acids such as citric acid, fumaric acid, maleic acid, tartaric acid, acetic acid, trifluoro acetic acid, benzoic acid, p-toluene sulphonic acid, methanesulphonic acid and naphthalene sulphonic acid.

The compounds of the invention of the general formula (1), as well as the salts thereof, have NK-1 antagonistic activity and show a good bioavailability. They are useful in the treatment of disorders in which neurokinins which interact with NK-1 receptors, e.g. neurokinin-1 (=Substance P) are involved, or that can be treated via manipulation of those receptors. For instance in acute and chronic pain, emesis, inflammatory diseases such as meningitis, arthritis, asthma, psoriasis and (sun)burns; gastro-intestinal disorders, in particular irritable bowel syndrome, inflammatory bowel disease (Crohn's disease), ulcerative colitis; bladder or GI tract hypermotility disorders, urinary tract inflammation; allergic responses such as eczema and rhinitis; cardiovascular disorders such as hypertension, atherosclerosis, edema, angina, cluster headache and migraine; cutaneous diseases such as urticaria, lupus erythematosus and pruritus; respiratory disorders including chronic obstructive pulmonary disease, bronchospams, bronchopneumonia, bronchitis, respiratory distress syndrome and cystic fibrosis; various neoplastic diseases; psychiatric and/or neurological disorders such as schizophrenia and other psychotic disorders; mood disorders such as bipolar I disorders, bipolar II disorders and unipolar depressive disorders like minor depression, seasonal affective disorder, postnatal depression dysthymia and major depression, anxiety disorders including panic disorder (with or without agoraphobia), social phobia, obsessive compulsive disorder (with or without co-morbid chronic tic or schizotypal disorder), posttraumatic stress disorder and generalized anxiety disorder; substance related disorders, including substance use disorders (like dependence and abuse) and substance induced disorders (like substance withdrawal); pervasive development disorders including autistic disorder and Rett's disorder; attention deficit and disruptive behavior disorders such as attention deficit hyperactivity disorder; impulse control disorders like agression, pathological gambling; eating disorders like anorexia nervosa and bulimia nervosa, obesity; sleep disorders like insomnia; tic disorders like Tourette's disorder; restless legs syndrome; disorders characterized by impairment of cognition and memory such as Alzheimer's disease, Creutzfeldt-Jacob disease, Huntington's disease, Parkinson's disease and neurorehabilitation (post-traumatic brain lesions)

The NK-1 antagonistic properties of the compounds of the invention were tested using the methods outlined below.

Pharmacological Methods

Receptor Binding for Human NK-1 Receptors

Affinity of the compounds for human NK-1 receptors was assessed using radioreceptor binding assays. Membrane preparations were prepared from Chinese Hamster Ovarium fibroblast (CHO) cells in which the human NK-1 receptor was stably expressed. Membranes were incubated with [$^3$H]-substance P in the absence or the presence of specified concentrations of the compounds, diluted in a suitable buffer in presence of peptidase inhibitor for 10 min at 25° C. Separation of bound radioactivity from free was done by filtration over Whatman GF/B glass fiber filters with two 5 sec washings. Bound radioactivity was counted by liquid scintillation counting using a Betaplate counter. Measured radioactivity was plotted against the concentration of the displacing test compound and displacement curves were calculated by four-parameter logistic regression, resulting in $IC_{50}$ values, i.e. that concentration of displacing compound by which 50% of the radioligand is displaced. Affinity $pK_1$ values were calculated by correcting the $IC_{50}$ values for radioligand concentration and its affinity for the human NK-1 receptor according to the Cheng-Prusoff equation:

$$pK_1 = -\log(IC_{50}/(1+S/K_d))$$

in which the $IC_{50}$ is as described above, S is the concentration [$^3$H]-substance P used in the assay expressed in mol/l, and $K_d$ is the equilibrium dissociation constant of [$^3$H]-substance P for human NK-1 receptors (in mol/l).

In Vitro Functional Methods for NK-1 Receptors

PI Metabolism

The effects of test compounds on the turnover of phosphatidyl-inositol (PI) was assessed in CHO cells, stably expressing the cloned human neurokinin NK-1 receptors. In these cells, NK-1 receptors are positively linked to phospholipase C, liberating inositolphosphates from membrane phospholipids. Inositiol phosphates can accumulate in cells when inositol-1-phosphatase is inhibited by preincubating cells with lithium. For tests, cells were cultured in 24-well plates and incubated overnight with [$^3$H]-myo-inositol which is metabolically incorporated in membrane phospholipids. After labeling, cells were rinsed twice with phosphate-buffered saline (pH 7.4) and incubated for 1 hr in α-DMEM. Thereafter, LiCl was added and 20 min later the test compounds were added to the incubation medium and incubated for 1 hr. Both LiCl and substance P in the absence or presence of test compounds (at specified concentrations) were diluted to appropriate concentrations in serum-free α-DMEM in such a way that LiCl had a final concentration of 5 mM.

After incubation, the medium was aspirated and cells were extracted with 5% trichloracetic acid. The inositol phosphates were recovered from the extract by sequential organic extraction using dichloromethane and water and ion-exchange chromatography over AG-1X2 DOWEX columns that were eluted by 1M ammonium formate (pH 7). Radioactivity in eluted fractions was counted using liquid scintillation counting and radioactivity was plotted against compound concentrations to construct concentration-effect relationships. Four-parameter logistic regression was done allowing estimates for potency and intrinsic activity of compounds.

$IC_{50}$ values, i.e. that compound concentration that antagonized 50% of substance P-induced accumulation of inositol phosphates, were obtained and antagonist potencies ($pA_2$) values were calculated using:

$$pA_2 = IC_{50}/(1+[SP]/EC_{50})$$

in which the $IC_{50}$ of the test compound was obtained from concentration-effect relationships, [SP] is the concentration of substance P (in mol/l; typically 1.0 nM), and the $EC_{50}$ is the potency of substance P at human cloned NK-1 receptors.

cAMP Measurements

The effects of test compounds at formation of cyclic AMP (cAMP) was assessed using CHO fibroblast cells, stably expressing cloned human NK-1 receptors. In addition to coupling to phospholipase C, human NK-1 receptors are also able to stimulate adenylate cyclase, which converts ATP into cAMP. For tests, cells were cultured in 24-well plates. Prior to experiments, medium was replaced by serum-free α-DMEM culture medium, containing [3H]-adenine which is taken up by the cells and converted sequentially into radiolabeled adenosine, AMP, ADP and ultimately into radiolabeled ATP. After 2 hrs, cells were rinsed twice with phosphate-buffered saline (pH 7.4) in presence of 1 mM isobutylmethylxanthine (IBMX; inhibitor of phosphodiesterases that hydrolyse cAMP into AMP). Subsequently, cells were stimulated by 10 nM substance P in absence or presence of test compounds in appropriate dilutions in PBS/IBMX for 20 min. After stimulation, medium was aspirated and cells were extacted by 5% trichloracetic acid. Radiolabeled ATP and cAMP were recovered from the extracts using sequential column chromatography. Extracts were separated by ion-exchange chromatography over DOWEX 50WX4 columns, allowing the recovery of ATP. Columns were subsequently put on top of aluminum oxide columns and eluted with water. Recovery of cAMP was performed by eluting the aluminum oxide columns with 100 mM imidazole (pH 7.4). Both ATP and cAMP fractions were counted for radioactivity using liquid scintillation counting and conversion ratios were calculated as:

$$v=[cAMP]*100\%/([ATP]+[cAMP]).$$

Concentration-response relationships were constructed by plotting cAMP conversion against compound concentration and $IC_{50}$ concentrations were calculated by four-parameter logistic regression. Antagonist potencies ($pA_2$) values were calculated using:

$$pA_2=IC_{50}/(1+[SP]/EC_{50})$$

in which the $IC_{50}$ of the test compound was obtained from concentration-effect relationships, [SP] is the concentration of substance P(in mol/l; typically 10 nM), and the $EC_{50}$ is the potency of substance P at human cloned NK-1 receptors.

NK-1 Agonist-induced Gerbil Foot-Tapping

The ability of NK-1 antagonists to antagonise foot-tapping induced by centrally administered NK-1 agonists has been demonstrated (IRupniak and Williams, 1994 (Eur. J. Pharmacol. 265:179); Bristow and Young, 1994 (Eur. J. Pharmacol. 254:–245)). Therefore, we have used this model to assess the in vivo activity of the compounds of the invention.

60 min prior to anaesthesia with $N_2O$ (0.8 L/min), halothane (3%) and; $O_2$ (0.8 L/min) male gerbils (40–60 g; Charles River) received an injection of vehicle or test compound (pars orale). Upon successful narcosis the anaesthetic was adjusted to $N_2O$ (0.6 L/min), halothane (1.5%) and $O_2$ (0.6 L/min) and a midline scalp incision made. GR 73632 was infused into the cerebroventricular space (AP— 0.5 mm, L—1.2 mm, and vertical—4.5 mm from bregma). Following recovery from anaesthesia (about 3–4 min) the foot tapping response was recorded for 5 minutes. The predefined criteria for the antagonism of this response was defined as inhibition of foot tapping for $\geq 5$ minutes.

The compounds of the invention have a high affinity for NK-1 receptors in the binding assay described above. The compounds of the invention are also active in the cAMP assay, their $pA_2$-values being in line with their $pK_1$-values. Some of the compounds belonging to the invention penetrate the blood brain barrier as is evident from their activity in the neurokinin-agonist induced gerbil foot tapping assay. This property makes them useful in the treatment of CNS disorders.

The invention is further illustrated by means of the following specific examples. These examples are only intended to further illustrate the invention, in more detail, and therefore are not deemed to restrict the scope of the invention in any way.

EXAMPLE 1

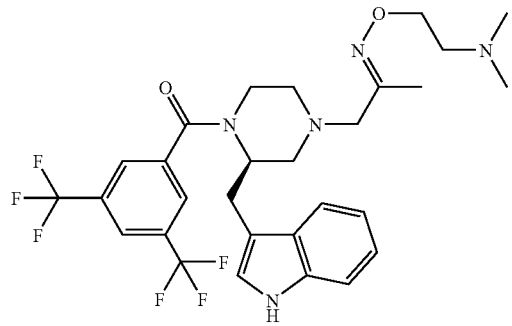

A mixture of (2R)-1-[3,5-bis(trifluoromethyl)benzoyl]-2-(1H-indol-3-ylmethyl)-4-(2-propanon-1-yl)piperazine (255 mg), O-[2-(dimethylamino)ethyl]hydroxylamine dihydrochloride (89 mg), sodium acetate (catalytically), and methanol (10 mL) was heated under reflux for 2 h. The solvent was removed in vacuo, and the residue was treated with dichloromethane and NAOH (aq, 2N). The layers were separated, the organic layer was dried and concentrated in vacuo. The residue was purified by flash chromatography ($SiO_2$, $CH_2Cl_2$/MeOH/$NH_4OH$ 92/7.5/0.5) to afford 1-{(2R)-1-[3,5-bis(trifluoromethyl)benzoyl]-2-(1H-indol-3-ylmethyl)-piperazin-4-yl}-2-propanone O-[2-(dimethylamino)-ethyl] oxime 0.31 g (>95%) as an E/Z mixture. $R_f$ 0.26 ($CH_2Cl_2$/MeOH/$NH_4OH$ 92/7.5/0.5).

The following compounds were obtained according to a similar manner:

1) 1-{(2R)-1-[3,5-bis(trifluoromethyl)benzoyl]-2-(1H-indol-3-ylmethyl)-piperazin-4-yl}-2-phenyl-2-ethanone O-[2-(morpholin-4-yl)ethyl]oxime. $MH^+$ 702; $R_f$ 0.27+ 0.34 (E+Z isomer) ($CH_2Cl_2$/MeOH 95/5).

2) 1-{(2R)-1-[3,5-bis(trifluoromethyl)benzoyl]-2-(1H-indol-3-ylmethyl)-piperazin-4-yl}-2-phenyl-2-ethanone O-[2-(dimethylamino)ethyl]oxime. $MH^+$ 660; $R_f$ 0.50 ($CH_2Cl_2$/MeOH/$NH_4OH$ 92/7.5/0.5).

3) 1-{(2R)-1-[3,5-bis(trifluoromethyl)benzoyl]-2-(1H-indol-3-ylmethyl)-piperazin-4-yl}-2-phenyl-2-ethanone O-[2-aminoethyl]oxime. $R_f$ 0.30 ($CH_2Cl_2$/MeOH/$NH_4OH$ 92/7.5/0.5).

4) 1-{(2R)-1-[3,5-bis(trifluoromethyl)benzoyl]-2-(1H-indol-3-ylmethyl)-piperazin-4-yl}-2-phenyl-2-ethanone O-[3-(morpholin-4-yl)propyl]oxime. $MH^+$ 716; $R_f$ 0.30 ($CH_2Cl_2$/MeOH 95/5).

4a) 1-{(2R)-1-[3,5-bis(trifluoromethyl)benzoyl]-2-(1H-indol-3-ylmethyl)-piperazin-4-yl}-2-phenyl-2-ethanone O-[3-(dimethylamino)propyl]oxime. $MH^+$ 674; $R_f$ 0.40 ($CH_2Cl_2$/MeOH/$NH_4OH$ 92/7.5/0.5).

5) 1-{(2R)-1-[3,5-bis(trifluoromethyl)benzoyl]-2-(1H-indol-3-ylmethyl)-piperazin-4-yl}-2-propanone O-methyloxime. $MH^+$ 541; $R_f$ 0.55 (EtOAc).

6) 1-{(2R)-1-[3,5-bis(trifluoromethyl)benzoyl]-2-(1H-indol-3-ylmethyl)-piperazin-4-yl}-2-propanone O-[2-(morpholin-4-yl)ethyl]oxime. $MH^+$ 640; $R_f$ 0.30 ($CH_2Cl_2$/MeOH 95/5).

7) 1-{(2R)-1-[3,5-bis(trifluoromethyl)benzoyl]-2-(1H-indol-3-ylmethyl)-piperazin-4-yl}-2-propanone O-[2-(1-thiomorpholin-4-yl)ethyl]oxime. $MH^+$ 656; $R_f$ 0.70 ($CH_2Cl_2$/MeOH/$NH_4OH$ 92/7.5/0.5).

8) 1-{(2R)-1-[3,5-bis(trifluoromethyl)benzoyl]-2-(1H-indol-3-ylmethyl)-piperazin-4-yl}-2-propanone O-[2-(4-

9) 1-{(2R)-1-[3,5-bis(trifluoromethyl)benzoyl]-2-(1H-indol-3-ylmethyl)-piperazin-4-yl}-2-propanone O-[2-aminoethyl]oxime. MH+ 570.

10) 1-{(2R)-1-[3,5-bis(trifluoromethyl)benzoyl]-2-(1H-indol-3-ylmethyl)-piperazin-4-yl}-2-propanone O-[2-(methylamino)ethyl]oxime. MH+ 584; $R_f$ 0.43 ($CH_2Cl_2$/MeOH/$NH_4OH$ 85/15/1).

11) 1-{(2R)-1-[3,5-bis(trifluoromethyl)benzoyl]-2-(1H-indol-3-ylmethyl)-piperazin-4-}-2-propanone O-[3-(morpholin-4-yl)propyl]oxime. $R_f$ 0.35 ($CH_2Cl_2$/MeOH 95/5).

12) 1-{(2R)-1-[3,5-bis(trifluoromethyl)benzoyl]-2-(1H-indol-3-ylmethyl)-piperazin-4-yl}-2-propanone O-[3-(dimethylamino)propyl]oxime. MH+ 611; $R_f$ 0.35 ($CH_2Cl_2$/MeOH/$NH_4OH$ 92/7.5/0.5).

13) 1-{(2R)-1-[3,5-bis(trifluoromethyl)benzoyl]-2-(1H-indol-3-ylmethyl)-piperazin-4-yl}-3-butanone O-[2-(dimethylamino)ethyl]oxime. MH+ 612; $R_f$ 0.10 ($CH_2Cl_2$/MeOH/$NH_4OH$ 93/7/0.5).

14) 1-{(2R)-1-[3,5-bis(trifluoromethyl)benzoyl]-2-(1H-indol-3-ylmethyl)-piperazin-4-yl}-3-butanone O-[2-(morpholin-4-yl)ethyl]oxime. MH+ 654; $R_f$ 0.37 ($CH_2Cl_2$/MeOH/$NH_4OH$ 9317/0.5).

15) 1-{(2R)-1-[3,5-bis(trifluoromethyl)benzoyl]-2-(1H-indol-3-ylmethyl)-piperazin-4-yl}-3-butanone O-[2-aminoethyl]oxime. MH+ 584; $R_f$ 0.16 ($CH_2Cl_2$/MeOH/$NH_4OH$ 93/7/0.5).

16) 1-{(2R)-1-[3,5-bis(trifluoromethyl)benzoyl]-2-(1H-indol-3-ylmethyl)-piperazin-4-yl}-3-butanone O-[3-(dimethylamino)propyl]oxime. MH+ 626; $R_f$ 0.20 ($CH_2Cl_2$/MeOH/$NH_4OH$ 93/7/0.5).

17) 1-{(2R)-1-[3,5-bis(trifluoromethyl)benzoyl]-2-(1H-indol-3-ylmethyl)-piperazin-4-yl}-3-butanone O[3-(morpholin-4-yl)propyl]oxime. MH+ 668; $R_f$ 0.50 ($CH_2Cl_2$/MeOH/$NH_4OH$ 93/7/0.5).

18) 1-{(2R)-1-[3,5-bis(trifluoromethyl)benzoyl]-2-(1H-indol-3-ylmethyl)-piperazin-4-yl}-4-pentanone O-[2-(morpholin-4-yl)ethyl]oxime. MH+ 668; $R_f$ 0.33 ($CH_2Cl_2$/MHeO 8/2).

19) 3-{(2R)-1-[3,5-bis(trifluoromethyl)benzoyl]-2-(1H-indol-3-ylmethyl)-piperazin-4-yl]-propanal O-[2-(dimethylamino)ethyl]oxime. MH+ 598; $R_f$ 0.29 ($CH_2Cl_2$/MeOH/$NH_4OH$ 93/7/0.5).

20) 3-{(2R)-1-[3,5-bis(trifluoromethyl)benzoyl]-2-(1H-indol-3-ylmethyl)-piperazin-4-yl]-propanal O-[2-(morpholin-4-yl)ethyl]oxime. MH+ 640; $R_f$ 0.33 ($CH_2Cl_2$/MeOH 9/1).

21) 1-{(2R)-1-[3,5-bis(trifluoromethyl)benzoyl]-2-(1H-indol-3-ylmethyl)-piperazin-4-yl}-3-phenyl-3-propanone O-[2-(morpholin-4-yl)ethyl]oxime. MH+ 716; $R_f$ 0.26 ($CH_2Cl_2$/MeOH/$NH_4OH$ 93/7/0.5).

22) 1-{(2R)-1-[3,5-bis(trifluoromethyl)benzoyl]-2-(1H-indol-3-ylmethyl)-piperazin-4-yl}-3-phenyl-3-propanone O-[3-(morpholin-4-yl)propyl]oxime. MH+ 730; $R_f$ 0.23 ($CH_2Cl_2$/MeOH 95/5).

23) 1-{(2R)-1-[3,5-bis(trifluoromethyl)benzoyl]-2-(1H-indol-3-ylmethyl)-piperazin-4-yl}-2-propanone O-[2-(2-pyridyl)ethyl]oxime. MH+ 632; $R_f$ 0.12 ($CH_2Cl_2$/MeOH 98/2).

24) 1-{2R)-1-[3,5-bis(trifluoromethyl)benzoyl]-2-(1H-indol-3-ylmethyl)-piperazin-4-yl}-2-propanone O-[2-pyridylmethyl]oxime. MH+ 618; $R_f$ 0.24 ($CH_2Cl_2$/MeOH 97/3).

25) 1-{2R)-1-[3,5-bis(trifluoromethyl)benzoyl]-2-(1H-indol-3-ylmethyl)-piperazin-4-}-2-propanone O-[3-pyridylmethyl]oxime. MH+ 618; $R_f$ 0.27 ($CH_2Cl_2$/MeOH 97/3).

26) 1-{2R)-1-[3,5-bis(trifluoromethyl)benzoyl]-2-(1H-indol-3-ylmethyl)-piperazin-4-yl}-2-propanone O-[4-pyridylmethyl]oxime. MH+ 618; $R_f$ 0.19 ($CH_2Cl_2$/MeOH 97/3).

27) 1-{(2R)-1-[3,5-difluorobenzoyl]-2-(1H-indol-3-ylmethyl)-piperazin-4-yl}-2-propanone O-[2-(morpholin-4-yl)ethyl]oxime. MH+ 540; $R_f$ 0.61 ($CH_2Cl_2$/MeOH/$NH_4OH$ 93/7/0.5).

28) 1-{(2R)-1-[3,5-dichlorobenzoyl]-2-(1H-indol-3-ylmethyl)-piperazin-4-yl}-2-propanone O-[2-(morpholin-4-yl)ethyl]oxime. MH+ 572; $R_f$ 0.20 ($CH_2Cl_2$MeH 95/5).

29) 1-{(2R)-1-[3,5-dibromobenzoyl]-2-(1H-indol-3-ylmethyl)-piperazin-4-yl}-2-propanone O-[2-(morpholin-4-yl)ethyl]oxime. MH+ 662; $R_f$ 0.44 ($CH_2Cl_2$/MeOH/$NH_4OH$ 93/7/0.5).

30) 1-{(2R)-1-[3,5-dicyanobenzoyl]-2-(1H-indol-3-ylmethyl)-piperazin-4-yl}-2-propanone O-[2-(morpholin-4-yl)ethyl]oxime. MH+ 554.

31) 1-{(2R)-1-[2-methoxy-5-(5-trifluoromethyltetrazol-1-yl)benzoyl]-2-(1H-indol-3-ylmethyl)-piperazin-4-yl}-2-propanone O-[2-(morpholin-4-yl)ethyl]oxime 32) 1-{(2R)-1-[3-fluoro-5-(trifluoromethyl)benzoyl]-2-(1H-indol-3-ylmethyl)-piperazin-4-yl}-2-propanone O-[2-(morpholin-4-yl)ethyl]oxime 33) 1-{(2R)-1-[(2,6-dichloropyridin-4-yl)carbonyl]-2-(1H-indol-3-ylmethyl)-piperazin-4-yl}-2-propanone O-[2-(morpholin-4-yl)ethyl]oxime 34) 1-{(2R)-1-[2,4-bis(trifluoromethyl)benzoyl]-2-(1H-indol-3-ylmethyl)-piperazin-4-yl}-2-propanone O-[2-(morpholin-4-yl)ethyl]oxime. MH+ 640; $R_f$ 0.74 ($CH_2Cl_2$/MeOH 97/3).

35) 1-{(2R)-1-[2,5-bis(trifluoromethyl)benzoyl]-2-(1H-indol-3-ylmethyl)-piperazin-4-yl}-2-propanone O-[2-(morpholin-4-yl)ethyl]oxime. MH+ 640; $R_f$ 0.64 ($CH_2Cl_2$/MeOH 97/3).

36) 1-{(2R)-1-[3,5-dimethylbenzoyl]-2-(1H-indol-3-ylmethyl)-piperazin-4-yl}-2-propanone O-[2-(morpholin-4-yl)ethyl]oxime. MH+ 532; $R_f$ 0.57 ($CH_2Cl_2$/MeOH 97/3).

37) 1-{(2R)-1-[2-chloro-5-(trifluoromethyl)benzoyl]-2-(1H-indol-3-ylmethyl)-piperazin-4-yl}-2-propanone O-[2-(morpholin-4-yl)ethyl]oxime. MH+ 606; $R_f$ 0.75 ($CH_2Cl_2$/MeOH 97/3).

38) 1-{(2R)-1-[2-methoxybenzoyl]-2-(1H-indol-3-ylmethyl)-piperazin-4-yl}-2-propanone O-[2-(morpholin-4-yl)ethyl]oxime. MH+ 534; $R_f$ 0.63 ($CH_2Cl_2$/MeOH 97/3).

39) 1-{1-[3,5-bis(trifluoromethyl)benzoyl]-2-(5-fluoro-1H-indol-3-ylmethyl)-piperazin-4-yl}-2-propanone O-[2-(morpholin-4-yl)ethyl]oxime. MH+ 658; $R_f$ 0.33 ($CH_2Cl_2$/MeOH 9/1).

40) 1-{1-[3,5-bis(trifluoromethyl)benzoyl]-2-(5-fluoro-1H-indol-3-ylmethyl)-perazin-4-yl}-2-propanone O-[2-(dimethylamino)ethyl]oxime. MH+ 616; $R_f$ 0.15 ($CH_2Cl_2$/MeOH 9/1).

41) 1-{1-[3,5-bis(trifluoromethyl)benzoyl]-2-(5-methyl-1H-indol-3-ylmethyl)-piperazin-4-yl}-2-propanone O-[2-(morpholin-4-yl)ethyl]oxime. MH+ 654; $R_f$ 0.22 ($CH_2Cl_2$/MeOH/$NH_4OH$ 92/7.5/0.5).

42) 1-{1-[3,5-bis(trifluoromethyl)benzoyl]-2-(5-methyl-1H-indol-3-ylmethyl)-piperazin-4-yl}-2-propanone O-[2-(dimethylamino)ethyl]oxime. MH+ 612; $R_f$ 0.09 ($CH_2Cl_2$/MeOH/$NH_4OH$ 92/7.5/0.5).

43) 1-{1-[3,5-bis(trifluoromethyl)benzoyl]-2-(7-aza-1H-indol-3-ylmethyl)-piperazin-4-yl}-2-propanone O-[2-(morpholin-4-yl)ethyl]oxime. MH⁺ 641; R_f 0.34 (CH₂Cl₂/MeOH 9/1).
44) 1-{1-[3,6-bis(trifluoromethyl)benzoyl]-2-benzyl-piperazin-4-yl}-2-propanone O-[2-(morpholin-4-yl)ethyl]oxime. MH⁺ 601; R_f 0.45 (CH₂Cl₂/MeOH 97/3).
45) 1-{1-[3,5-bis(trifluoromethyl)benzoyl]-2-(1H-indol-2-ylmethyl)-piperazin-4-yl}-2-propanone O-[2-(morpholin-4-yl)ethyl]oxime. MH⁺ 640; R_f 0.46 (CH₂Cl₂/MeOH/NH₄OH 93/7/0.5).
46) 1-{(2R)-1-[3,5-bis(trifluoromethyl)benzoyl]-2-(1H-indol-3-ylmethyl)-piperazin-4-yl}-2-propanone O-[2-(morpholin-4-yl)-2-oxo-ethyl]oxime. R_f 0.25 (CH₂Cl₂/MeOH 97/3).
47) 1-{(2R)-1-[3,5-bis(trifluoromethyl)benzoyl]-2-(1H-indol-3-ylmethyl)-piperazin-4-}-2-propanone O-[2-(morpholin-4-yl)propyl]oxime. MH⁺ 654; R_f 0.19 (CH₂Cl₂/MeOH 97/3).
48) 1-{(2R)-1-[3,5-bis(trifluoromethyl)benzoyl]-2-(1H-indol-3-ylmethyl)-piperazin-4-yl}-2-propanone O-[2-methyl-2-(morpholin-4-yl)propyl]oxime. MH⁺ 668; R_f 0.45 (CH₂Cl₂/MeOH 97/3).
49) 1-{(2R)-1-[3,5-bis(trifluoromethyl)benzoyl]-2-(1H-indol-3-ylmethyl)-piperazin-4-yl}-2-propanone O-[2-(2,6-dimethyl-morpholin-4-yl)ethyl]-oxime. MH⁺ 668; R_f 0.34 (CH₂Cl₂/MeOH/NH₄OH 96/3.75/0.25).
50) 1-{(2R)-1-[3,5-bis(trifluoromethyl)benzoyl]-2-(1H-indol-3-ylmethyl)-piperazin-4-yl}-2-propanone O-[2-(1,1-dioxo-1-thiomorpholin-4-yl)ethyl]oxime. MH⁺ 688; R_f 0.34 (CH₂Cl₂/MeOH/NH₄OH 96/3.75/0.25).
51) 1-{(2R)-1-[3,5-bis(trifluoromethyl)benzoyl]-2-(1H-indol-3-ylmethyl)-piperazin-4-yl}-2-propanone O-[2-(3,5-dimethyl-morpholin-4-yl)ethyl]-oxime (Isomer 1). MH⁺ 668; R_f 0.20+0.28 (E+Z isomer) (CH₂Cl₂/MeOH/NH₄OH 96/3.75/0.25).
52) 1-{(2R)-1-[3,5-bis(trifluoromethyl)benzoyl]-2-(1H-indol-3-ylmethyl)-piperazin-4-yl}-2-propanone O-[2-(3,5-dimethyl-morpholin-4-yl)-ethyl]-oxime (Isomer 2). MH⁺ 668; R_f 0.21+0.31 (E+Z isomer) (CH₂Cl₂/MeOH/NH₄OH 96/3.75/0.25).
53) 1-{(2R)-1-[3,5-bis(trifluoromethyl)benzoyl]-2-(1H-indol-3-ylmethyl)-piperazin-4-yl}-2-propanone O-[2-(3-methoxymethyl-morpholin-4-yl)ethyl]-oxime. MH⁺ 684; R_f 0.46+0.54 (E+Z isomer) (CH₂Cl₂/MeOH/NH₄OH 92/7.5/0.5).
54) 1-{(2R)-1-[3,5-bis(trifluoromethyl)benzoyl]-2-(1H-indol-3-ylmethyl)-piperazin-4-yl}-2-propanone O-[2-(cis-3,5-bis-methoxymethyl-morpholin-4-yl)ethyl]-oxime. R_f 0.17+0.23 (E+Z isomer) (CH₂Cl₂/MeOH/NH₄OH 96/3.75/0.25).
55) 1-{(2R)-1-[3,5-bis(trifluoromethyl)benzoyl]-2-(1H-indol-3-ylmethyl)-piperazin-4-yl}-2-propanone O-[2-(trans-3,5-bis-methoxymethyl-morpholin-4-yl)ethyl]-oxime. MH⁺ 728.
56) 1-{1-[3,5-bis(trifluoromethyl)benzoyl]-2-(4-chlorobenzyl)-piperazin-4-yl}-2-propanone O-[2-(morpholin-4-yl)ethyl]oxime. MH⁺ 635; R_f 0.28 (CH₂Cl₂/MeOH 95/5).
57) 1-{1-[3,5-bis(trifluoromethyl)benzoyl]-2-(3,4-dichlorobenzyl)-piperazin-4-yl}-2-propanone O-[2-(morpholin-4-yl)ethyl]oxime. MH⁺ 669; R_f 0.63 (CH₂Cl₂/MeOH 95/5).
58) 1-{1-[3,5-bis(trifluoromethyl)benzoyl]-2-(naphthalen-2-ylmethyl)-piperazin-4-yl}-2-propanone O-[2-(morpholin-4-yl)ethyl]oxime. MH⁺ 651; R_f 0.65 (CH₂Cl₂/MeOH/NH₄OH 93/7/0.5).
59) 1-{2-(benzo[b]thiophen-3-ylmethyl)-1-[3,5-bis(trifluoromethyl)benzoyl]-piperazin-4-yl}-2-propanone O-[2-(morpholin-4-yl)ethyl]oxime. MH⁺ 657; R_f 0.30 (CH₂Cl₂/MeOH 95/5).
60) 1-{1-[3,5-bis(trifluoromethyl)benzoyl]-2-(1H-indazol-3-ylmethyl)-piperazin-4-yl}-2-propanone O-[2-(morpholin-4-yl)ethyl]oxime. MH⁺ 641; R_f 0.40 (CH₂Cl₂/MeOH/NH4OH 93/7/0.5).
61) 1-{2-(benzofuran-2-ylmethyl)-1-[3,5-bis(trifluoromethyl)benzoyl]-piperazin-4-yl}-2-propanone O-[2-(morpholin-4-yl)ethyl]oxime. MH⁺ 641; R_f 0.30 (CH₂Cl₂/MeOH 95/5).

EXAMPLE 2

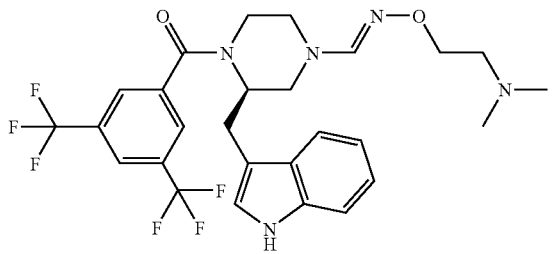

A mixture of (2R)-1-[3,5-bis(trifluoromethyl)benzoyl]-2-(1H-indol-3-ylmethyl)-piperazine (0.47 g), N,N-dimethylformamide dimethyl acetal (0.12 g), and acetonitrile 15 mL) was heated under reflux for 24 h. After cooling to room temperature the volatiles were removed in vacuo. The residue was dissolved in dry tetrahydrofuran, O-[2-(dimethylamino)ethyl]hydroxylamine dihydrochloride (547 mg) and diisopropylethylamine (1.1 mL) were added, and the resulting mixture was heated under reflux for two hours. The solvent was removed in vacuo and the residue was purified by flash chromatography (SiO₂, CH₂Cl₂/MeOH/NH₄OH 85/15/1) to afford 1-{(2R)-1-[3,5-bis(trifluoromethyl)benzoyl]-2-(1H-indol-3-ylmethyl)-piperazin-4-yl}-methanone O-[2-(dimethylamino)ethyl]oxime 0.79 g as an E/Z mixture. MH⁺ 570, R_f 0.32+0.49 (E+Z isomer) (CH₂Cl₂/MeOH/NH₄OH 85/15/1).

EXAMPLE 3

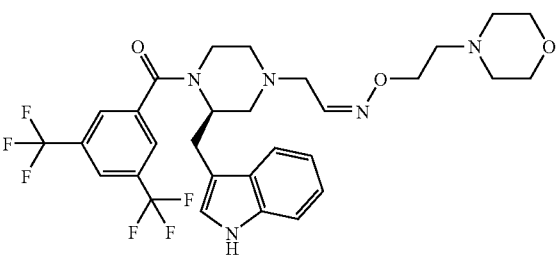

A mixture of 2-chloroethanal O-[2-(morpholin-4-yl)ethyl]oxime (0.13 g), (2R)-1-[3,5-bis(trifluoromethyl)-benzoyl]-2-(1H-indol-3-ylmethyl)piperazine (0.29 g), diisopropylethylamine (0.11 mL), and acetonitrile (10 mL) was heated under reflux overnight. After cooling to room temperature the solvent was removed in vacuo, and the residue treated with dichloromethane and K₂CO₃ (aq). The layers were separated, the organic layer was dried (Na$_2$SO$_4$), and concentrated in vacuo. The residue was purified by flash chromatography (SiO$_2$, CH$_2$Cl$_2$/MeOH/NH$_4$OH 92/7.5/0.5) to afford 2-{(2R)-1-[3,5-bis(trifluoromethyl)benzoyl]-2-(1H-indol-3-ylmethyl)-piperazin-4-yl}-ethanal O-[2-(morpholin-4-yl)ethyl]oxime 0.38 g (95%) as an E/Z mixture. MH$^+$ 626, R$_f$ 0.53+0.66 (E+Z isomer) (CH$_2$Cl$_2$/MeOH/NH$_4$OH 92/7.5/0.5).

The following compounds were obtained according to a similar manner:
1) 2-{(2R)-1-[3,5-bis(trifluoromethyl)benzoyl]-2-(1H-indol-3-ylmethyl)-piperazin-4-yl}-ethanal O-[3-(morpholin-4-yl)propyl]oxime. R$_f$ 0.63+0.72 (E+Z isomer) (CH$_2$Cl$_2$/MeOH/NH$_4$OH 92/7.5/0.5).
2) (2R)-1-[3,5-bis(trifluoromethyl)benzoyl]-2-(1H-indol-3-ylmethyl)-4-{[5-((morpholin-4-yl)-methyl)-4,5-dihydro-isoxazol-3-yl]-methyl}-piperazine. MH$^+$ 638, Two isomers isolated R$_f$ 0.51 (isomer 1) R$_f$ 0.61 (isomer 2) (CH$_2$Cl$_2$/MeOH/NH$_4$OH 96/3.75/0.25)
3) (2R)-1-[3,5-bis(trifluoromethyl)benzoyl]-2-(1H-indol-3-ylmethyl)-4-{[5-((morpholin-4-yl)-methyl)-isoxazol-3-yl]-methyl}-piperazine. Isolated as HCl-salt: mp 182–184° C., MH$^+$ 636, R$_f$ 0.28 (CH$_2$Cl$_2$/MeOH/NH$_4$OH 96/3.75/0.25).

EXAMPLE 4

Preparation of Intermediates Having Formula (2)

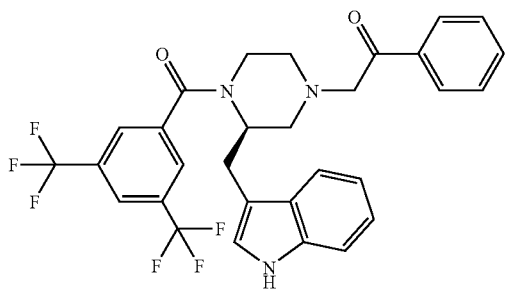

A mixture of phenacyl bromide (0.88 g), (2R)-1-[3,5-bis(trifluoromethyl)benzoyl]-2-(1H-indol-3-ylmethyl)piperazine (2 g), potassium iodide (catalytical), diisopropyl-ethylamine (0.77 mL), and acetonitrile (20 mL) was stirred at room temperature overnight. After cooling to room temperature the solvent was removed in vacuo, and the residue treated with dichloromethane and NaOH (2N). The layers were separated, the organic layer was dried (Na$_2$SO$_4$), and concentrated in vacuo. The residue was purified by flash chromatography (SiO$_2$, CH$_2$Cl$_2$/MeOH 97/3) to afford (2R)-1-[3,5-bis(trifluoromethyl)benzoyl]-2-(1H-indol-3-ylmethyl)-4-(2-phenyl-2-ethanon-1-yl)piperazine 2.16 g (85%). MH$^+$ 574, R$_f$ 0.44 (CH$_2$Cl$_2$/MeOH 97/3).

The following compounds were obtained according to a similar manner:
(2R)-1-[3,5-bis(trifluoromethyl)benzoyl]-2-(1H-indol-3-ylmethyl)-4-(2-propanon-1-yl)piperazine. MH$^+$ 512, R$_f$ 0.38 (CH$_2$Cl$_2$/MeOH 97/3).
(2R)-1-[3,5-difluorobenzoyl]-2-(1H-indol-3-ylmethyl)-4-(2-propanon-1-yl)piperazine. R$_f$ 0.72 (CH$_2$Cl$_2$/MeOH/NH$_4$OH 93/7/0.5).
(2R)-1-[3,5-dichlorobenzoyl]-2-(1H-indol-3-ylmethyl)-4-(2-propanon-1-yl)piperazine. R$_f$ 0.50 (CH$_2$Cl$_2$/MeOH/NH$_4$OH 93/7/0.5).
(2R)-1-[3,5-dibromobenzoyl]-2-(1H-indol-3-ylmethyl)-4-(2-propanon-1-yl)piperazine
(2R)-1-[2-methoxy-5-(5-trifluoromethyltetrazol-1-yl)benzoyl]-2(1H-indol-3-ylmethyl)-4-(2-propanon-1-yl)piperazine
(2R)-1-[3-fluoro-5-(trifluoromethyl)benzoyl]-2-(1H-indol-3-ylmethyl)-4-(2-propanon-1-yl)piperazine
(2R)-1-[(2,6-dichloropyridin-4-yl)carbonyl]-2-(1H-indol-3-ylmethyl)-4-(2-propanon-1-yl)piperazine
(2R)-1-[3,5-dicyanobenzoyl]-2-(1H-indol-3-ylmethyl)-4-(2-propanon-1-yl)piperazine
(2R)-1-[2,4-bis(trifluoromethyl)benzoyl]-2-(1H-indol-3-ylmethyl)-4-(2-propanon-1-yl)piperazine
(2R)-1-[3,5-dimethylbenzoyl]-2-(1H-indol-3-ylmethyl)-4-(2-propanon-1-yl)piperazin
(2R)-1-[2-chloro-5-(trifluoromethyl)benzoyl]-2-(1H-indol-3-ylmethyl)-4-(2-propanon-1-yl)piperazine
(2R)-1-[2,5-bis(trifluoromethyl)benzoyl]-2-(1H-indol-3-ylmethyl)-4-(2-propanon-1-yl)piperazine
(2R)-1-[2-methoxybenzoyl]-2-(1H-indol-3-ylmethyl)-4-(2-propanon-1-yl)piperazine
1-[3,5-bis(trifluoromethyl)benzoyl]-2-benzyl-4-(2-propanon-1-yl)piperazine. MH$^+$ 473, R$_f$ 0.65 (CH$_2$Cl$_2$/MeOH 97/3).
1-[3,5-bis(trifluoromethyl)benzoyl]-2-(4-chlorobenzyl)-4-(2-propanon-1-yl)piperazine. MH$^+$ 507, R$_f$ 0.89 (CH$_2$Cl$_2$/MeOH 95/5).
1-[3,5-bis(trifluoromethyl)benzoyl]-2-(3,4-dichlorobenzyl)-4-(2-propanon-1-yl)piperazine. R$_f$ 0.63 (CH$_2$Cl$_2$/MeOH 95/5).
1-[3,5-bis(trifluoromethyl)benzoyl]-2-(naphthalen-2-ylmethyl)-4-(2-propanon-1-yl)piperazine. R$_f$ 0.77 (CH$_2$Cl$_2$/MeOH 95/5).
1-[3,5-bis(trifluoromethyl)benzoyl]-2-(1H-indol-2-ylmethyl)-4-(2-propanon-1-yl)piperazine
1-[3,5-bis(trifluoromethyl)benzoyl]-2-(5-fluoro-1H-indol-3-ylmethyl)-4-(2-propanon-1-yl)piperazine
1-[3,5-bis(trifluoromethyl)benzoyl]-2-(5-methyl-1H-indol-3-ylmethyl)-4-(2-propanon-1-yl)piperazine. MH$^+$ 526; R$_f$ 0.52 (CH$_2$Cl$_2$/MeOH/NH$_4$OH 92/7.5/0.5).
1-[3,5-bis(trifluoromethyl)benzoyl]-2-(7-aza-1H-indol-3-ylmethyl)-4-(2-propanon-1-yl)piperazine. MH$^+$ 513; R$_f$ 0.38 (CH$_2$Cl$_2$/MeOH/NH$_4$OH 93/7/0.5).
1-[3,5-bis(trifluoromethyl)benzoyl]-2-(1H-indazol-3-ylmethyl)-4-(2-propanon-1-yl)piperazine; MH$^+$ 513; R$_f$ 0.32 (CH$_2$Cl$_2$/MeOH/NH$_4$OH 93/7/0.5).
2-(benzo[b]thiophen-3-ylmethyl)-1-[3,5-bis(trifluoromethyl)benzoyl]-4-(2-propanon-1-yl)piperazine. R$_f$ 0.73 (CH$_2$Cl$_2$/MeOH 9515).
2-(benzofuran-2-ylmethyl)-1-[3,5-bis(trifluoromethyl)benzoyl]-4-(2-propanon-1-yl)piperazine.
(2R)-1-[3,5-bis(trifluoromethyl)benzoyl]-2-(1H-indol-3-ylmethyl)-4-(3-phenyl-3-propanon-1-yl)piperazine. MH$^+$ 588, R$_f$ 0.50 (CH$_2$Cl$_2$/MeOH 95/5).
(2R)-1-[3,5-bis(trifluoromethyl)benzoyl]-2-(1H-indol-3-ylmethyl)-4-(3-butanon-1-yl)piperazine

EXAMPLE 5

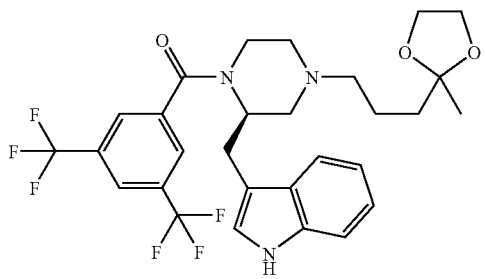

A mixture of 5-chloro-2-pentanone ethylene ketal (0.54 g), (2R)-1-[3,5-bis(trifluoro-methyl)benzoyl]-2-(1H-indol-3-ylmethyl)piperazine (1.37 g), diisopropylethylamine (0.6 mL), and dimethylformamide (25 mL) was heated overnight, at 90°C. After cooling to room temperature the mixture was poured in water and extracted with ethyl acetate. The organic layer was dried ($Na_2SO_4$), and concentrated in vacuo. The residue was purified by flash chromatography ($SiO_2$, $CH_2Cl_2$/MeOH 95/15) to afford (2R)-1-[3,5-bis(trifluoromethyl)benzoyl]-2-(1H-indol-3-ylmethyl)-4-[3-(2-methyl-1,3-dioxolan-2-yl)propyl]piperazine (0.7 g, 40%). $MH^+$ 584.

The following compound was obtained according to a similar manner:
(2R)-1-[3,5-bis(trifluoromethyl)benzoyl]-2-(1H-indol-3-ylmethyl)-4-2-(1,3-dioxolan-2-yl)ethyl]piperazine. $R_f$ 0.30 ($CH_2Cl_2$/MeOH/$NH_4OH$ 93/7/0.5).

EXAMPLE 6

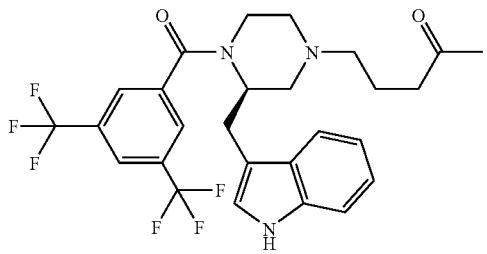

A mixture of (2R)-1-[3,5-bis(trifluoromethyl)benzoyl]-2-(1H-indol-3-ylmethyl)-4-[3-2-methyl-1,3-dioxolan-2-yl)propyl]piperazine (0.7 g), 1,4-dioxane (6 mL), and hydrochloric acid (6N, 5 mL) was heated at 50° C. for 2 h. After cooling to room temperature the mixture was poured into ammonium hydroxide and extracted with ethyl acetate. The organic layer was dried and concentrated in vacuo to afford crude (2R)-1-[3,5-bis(trifluoromethyl)benzoyl]-2-(1H-indol-3-ylmethyl)-4-(4-pentanon-1-yl)piperazine which was used as such. $MH^+$ 540, $R_f$ 0.51 ($CH_2Cl_2$/MeOH/$NH_4OH$ 93/7/0.5).

The following compound was obtained according to a similar manner:
(2R)-1-[3,5-bis(trifluoromethyl)benzoyl]-2-(1H-indol-3-ylmethyl)-4-(3-propanal-1-yl)piperazine. $R_f$ 0.33 ($CH_2Cl_2$/MeOH 95/5).

EXAMPLE 7

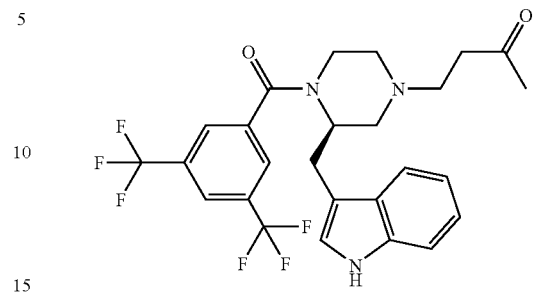

To a solution of (2R)-1-[3,5-bis(trifluoromethyl)benzoyl]-2-(1H-indol-3-ylmethyl)-4-(4-pentanon-1-yl)piperazine (1.37 g) in toluene (15 mL) was added drop-wise methyl vinyl ketone (0.3 g). After 2.5 h at room temperature the solution was concentrated to afford crude (2R)-1-[3,5-bis(trifluoromethyl)-benzoyl]-2-(1H-indol-3-ylmethyl)-4-(3-butanon-1-yl)piperazine which was used as such. $R_f$ 0.55 ($CH_2Cl_2$/MeOH 95/5).

EXAMPLE 8

Preparation of Intermediates Having Formula (7)

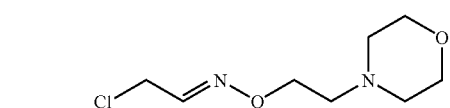

A mixture of acetaldehyde (0.1 mL of a 50 wt % soln. in water), O-[2-((morpholin-4-yl))ethyl]hydroxylamine dihydrochloride (0.14 g), NaOH (2N, 0.64 mL) and water (5 mL) was stirred at room temperature overnight. The solution was made basic with NaOH (1N) and extracted with dichloromethane. The organic layer was dried ($Na_2SO_4$), and concentrated in vacuo to afford 2-chloroethanal O-[2-((morpholin-4-yl))ethyl]oxime (0.13 g, ~100%), which was used as such.

The following compound was obtained according to a similar manner:
2-chloroethanal O-[3-((morpholin-4-yl))propyl]oxime

EXAMPLE 9

Preparation of Intermediates Having Formula (9)

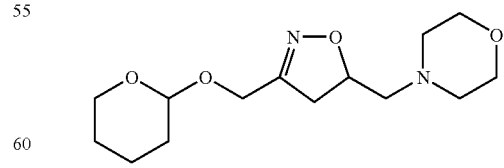

To a solution of N-allylmorpholine (0.76 g, 5.0 mmol) in toluene (10 mL) was added 2-(2-nitroethoxy)tetrahydropyran (1.34 g, 7.7 mmol), phenylisocyanate (2:43 g, 20.1 mmol), and triethylamine (52 mg; 0.5 mmol). The resulting mixture was heated at 55° C. overnight. After cooling to room temperature the formed precipitate was removed by filtration and the remaining solution concentrated in vacuo. The residue was purified by flash chromatography (SiO$_2$, CH$_2$Cl$_2$/MeOH/NH$_4$OH 96/3.75/0.25) to yield 0.63 g (44%) of [5-((morpholin-4-yl)methyl)-4,5-dihydro-isoxazol-3-yl] methyl 2-tetrahydropyranyl ether. MH$^+$ 285, R$_f$ 0.34 (CH$_2$Cl$_2$/MeOH/NH$_4$OH 96/3.75/0.25).

The following compound was obtained according to a similar manner:
[5-((morpholin-4-yl)methyl)isoxazol-3-yl]methyl 2-tetrahydropyranyl ether. R$_f$ 0.18 (EtOAc/MeOH 99/1).

EXAMPLE 10

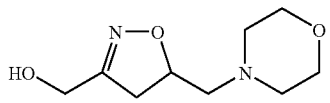

A mixture of [5-((morpholin-4-yl)methyl)-4,5-dihydro-isoxazol-3-yl]methyl 2-tetrahydropyranyl ether (0.63 g) with pyridinium p-toluenesulfonate (10 mol %) in methanol was heated under reflux for 24 h. After cooling to room temperature the solvent was removed in vacuo and the residue purified by flash chromatography (SiO$_2$, CH$_2$Cl$_2$/MeOH/NH$_4$OH 92/7.5/0.5) to afford [5-((morpholin-4-yl)methyl)-4,5-dihydro-isoxazol-3-yl]methanol (95%). R$_f$ 0.17 (CH$_2$Cl$_2$/MeOH/NH$_4$OH 92/7.5/0.5).

EXAMPLE 11

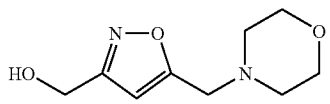

[5-((morpholin-4-yl)methyl)isoxazol-3-yl]methyl 2-tetrahydropyranyl ether (1.0 g) was dissolved in methanol (2 mL) and treated with 1 M HCl (aq. 10 mL). The mixture was stirred at room temperature for 1 h, then basified with K$_2$CO$_3$, and extracted with dichloromethane. The organic layers were dried (Na$_2$SO$_4$), and concentrated in vacuo. The residue was purified by flash chromatography (SiO$_2$, CH$_2$Cl$_2$/MeOH/NH$_4$OH 92/7.5/0.5) to afford [5-((morpholin-4-yl)methyl)-isoxazol-3-yl]methanol (53%). MH$^+$ 199, R$_f$ 0.24 (CH$_2$Cl$_2$/MeOH/NH$_4$OH 92/7.5/0.5).

EXAMPLE 12

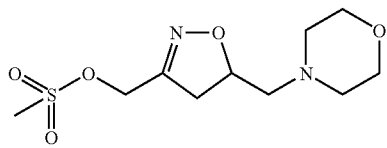

To a solution of [5-(morpholin-4-ylmethyl)-4,5-dihydro-isoxazol-3-yl]methanol (0.38 g) in dichloromethane was added dropwise diisopropylethylamine (0.33 mL) and methanesulfonyl chloride (0.15 mL). The resulting solution was stirred at room temperature for 3 h and treated with water. The layers were separated and the organic layer was dried (Na$_2$SO$_4$) en concentrated in vacuo to afford [5-((morpholin-4-yl)methyl)-4,5-dihydro-isoxazol-3-yl]methanol methanesulfonate, 0.52 g (~100%). R$_f$ 0.63 (CH$_2$Cl$_2$/MeOH/NH$_4$OH 92/7.5/0.5).

The following compound was obtained according to a similar manner:
[5-((morpholin-4-yl)methyl)isoxazol-3-yl]methanol methanesulfonate. R$_f$ 0.62 (CH$_2$Cl$_2$/MeOH/NH$_4$OH 96/3.75/0.25).

EXAMPLE 13

Preparation of Intermediates Having Formula (3)

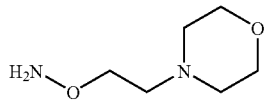

To a solution of acetophenone oxime (20 g) in toluene (700 mL) was added subsequently tetrabutylammonium bromide (4.77 g), water (8 mL), 4-(2-chloroethyl)morpholine hydrochloride (30.31 g) and finally 50% sodium hydroxide (aq, 52 mL). The resulting mixture was heated at 75° C. overnight. After cooling to room temperature water was added, to dissolve all the salts, the layers were separated, and the aqueous layer was extracted with toluene. The organic layers were dried (MgSO$_4$), and concentrated in vacuo. The residue was purified by flash chromatography (SiO$_2$, CH$_2$Cl$_2$/MeOH 95/5) to afford acetophenone O-[2-((morpholin-4-yl))ethyl]oxime as an oil. The obtained oil was dissolved in 6M HCl (aq, 500 mL) and heated under reflux for 5 hours and subsequently stirred overnight at room temperature. The mixture was extracted with ether and concentrated in vacuo. The residue was crystallized from ethanol, to afford O-[2-((morpholin-4-yl))ethyl]hydroxylamine dihydrochloride. 24.8 g (77%)

The following compounds were obtained according to a similar manner:
O-[2-(dimethylamino)ethyl]hydroxylamine dihydrochloride
O-[2-(methylamino)ethyl]hydroxylamine dihydrochloride
O-[3-(dimethylamino)propyl]hydroxylamine dihydrochloride
O-[3-((morpholin-4-yl))propyl]hydroxylamine dihydrochloride
O-[2-pyridylmethyl]hydroxylamine dihydrochloride
O-[3-pyridylmethyl]hydroxylamine dihydrochloride
O-[4-pyridylmethyl]hydroxylamine dihydrochloride

EXAMPLE 14

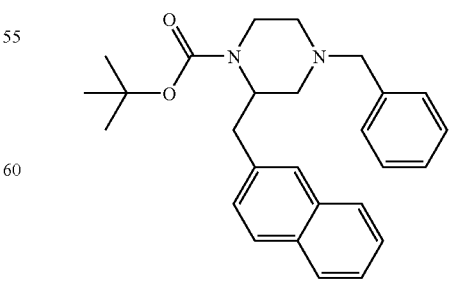

To a solution of 4-benzyl-piperazine-1-carboxylic acid tert-butyl ester (2 g) in diethylether (35 mL) was added tetramethylethylenediamine (1.4 mL). The resulting mixture was cooled to −70° C. and sec-butyllithium (7 mL of a 1.3 M solution) was added dropwise, after complete addition the solution was slowly warmed to −10° C., at which temperature the mixture was stirred for one hour. Subsequently, the mixture was recooled to −70° C.; then a solution of 2-(bromomethyl)naphthalene (2 g) in diethylether was added dropwise and stirring continued at −70° C. was continued for one hour. The resulting mixture was stirred and allowed to come to room temperature overnight, then partitioned between saturated ammonium chloride (aq) and ethyl acetate. The organic layer was dried over magnesium sulphate, filtered, and concentrated in vacuo. The residue was purified by flash chromatography (SiO$_2$, CH$_2$Cl$_2$/MeOH 99/1) to afford 4-benzyl-2-(naphthalen-2-ylmethyl)piperazine-1-carboxylic acid tert-butyl ester as an oil. 0.8 g (27 %) R$_f$ 0.47 (CH$_2$Cl$_2$/MeOH 99/1), MH$^+$ 417.

The following compounds were obtained according to a similar manner:

2-(7-aza-1-(toluene-4-sulfonyl)-1H-indol-3-ylmethyl)-4-benzylpiperazine-1-carboxylic acid tert-butyl ester; R$_f$ 0.28 (CH$_2$Cl$_2$/MeOH 99/1).

2,4-dibenzylpiperazine-1-carboxylic acid tert-butyl ester; MH$^+$ 367, R$_f$ 0.84 (CH$_2$Cl$_2$/MeOH/NH$_4$OH 93/7/0.5).

4-benzyl-2-(1-(toluene-4-sulfonyl)-1H-indol-2-ylmethyl)piperazine-1-carboxylic acid tert-butyl ester; MH$^+$ 560, R$_f$ 0.70 (CH$_2$Cl$_2$/MeOH 95/5). 4-benzyl-2-(4-chlorobenzyl)piperazine-1-carboxylic acid tert-butyl ester; MH$^+$ 401, R$_f$ 0.26 (CH$_2$Cl$_2$/MeOH 99/1).

4-benzyl-2-(3,4-dichlorobenzyl)piperazine-1-carboxylic acid tert-butyl ester; R$_f$ 0.77 (CH$_2$Cl$_2$/MeOH/NH$_4$OH 93/7/0.5).

2-(benzo[b]thiophen-3-ylmethyl)-4-benzylpiperazine-1-carboxylic acid tert-butyl ester; MH$^+$ 423; R$_f$ 0.30 (CH$_2$Cl$_2$/MeOH 99/1).

3-(4-benzyl-1-tert-butoxycarbonyl-piperazin-2-ylmethyl)-indazole-1-carboxylic acid tert-butyl ester; MH$^+$ 507.

2-(benzofuran-2-ylmethyl)-4-benzylpiperazine-1-carboxylic acid tert-butyl ester; MH$^+$ 407, R$_f$ 0.33 (CH$_2$Cl$_2$/MeOH 99/1).

EXAMPLE 15

Preparation of Intermediates Having Formula (10)

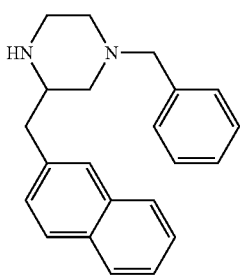

To a solution of 4-benzyl-2-(naphthalen-2-ylmethyl)piperazine-1-carboxylic acid tert-butyl ester (0.75 g) in dichloromethane (3 mL) was added dropwise trifluoroacetic acid (3 mL). After 75 min at room temperature the mixture was poured onto ice and made basic by the addition of ammonium hydroxide (25% solution). The layers were separated and the aqueous layer extracted with dichloromethane. The combined organic layers were dried over magnesium sulphate, filtered, and concentrated in vacuo to afford 1-benzyl-3-(naphthalen-2-ylmethyl)piperazine as an oil; 053 g (93%) MH$^+$ 317, R$_f$ 0.61 (CH$_2$Cl$_2$/MeOH/NH$_4$OH 93/7/0.5), which was used as such.

The following compounds were obtained according to a similar manner:

3-(7-aza-1-(toluene-4-sulfonyl)-1H-indol-3-ylmethyl)-1-benzylpiperazine, R$_f$ 0.13 (CH$_2$Cl$_2$/MeOH 95/5).

1,3-dibenzylpiperazine piperazine; MH$^+$ 267, R$_f$ 0.19 (CH$_2$Cl$_2$/MeOH/NH$_4$OH 93/7/0.5).

1-benzyl-3-(1-(toluene-4-sulfonyl)-1H-indol-2-ylmethyl)piperazine; MH$^+$ 460, R$_f$ 0.56 (CH$_2$Cl$_2$/MeOH/NH$_4$OH 93/7/0.5).

1-benzyl-3-(4-chlorobenzyl)piperazine; MH$^+$ 301, R$_f$ 0.26 (CH$_2$Cl$_2$/MeOH/NH$_4$OH 95/4.5/0.5).

1-benzyl-3-(3,4-dichlorobenzyl)piperazine; MH$^+$ 335, R$_f$ 0.35 (CH$_2$Cl$_2$/MeOH/NH$_4$OH 93/7/0.5).

3-(benzo[b]thiophen-3-ylmethyl)-1-benzylpiperazine; MH$^+$ 323, R$_f$ 0.35 (CH$_2$Cl$_2$/MeOH/NH$_4$OH 95/4.5/0.5).

1-benzyl-3-(1H-indazol-3-ylmethyl)piperazine; MH$^+$ 307, R$_f$ 0.10 (CH$_2$Cl$_2$/MeOH 9/1).

3-(benzofuran-2-ylmethyl)-1-benzylpiperazine; MH$^+$ 307, R$_f$ 0.26 (CH$_2$Cl$_2$/MeOH/NH$_4$OH 93/7/0.5).

EXAMPLE 16

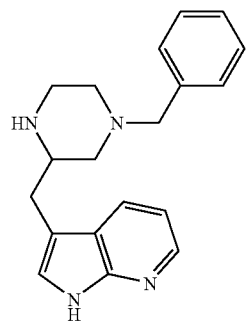

To a solution of 3-(7-aza-1-(toluene-4-sulfonyl)-1H-indol-3-ylmethyl)-1-benzyl-piperazine (0.65 g) in methanol (28 mL) was added 3 M aqueous sodium hydroxide (5.6 mL), and the resulting mixture was heated for 90 min at 60° C. After cooling to room temperature, most of the methanol was removed in vacuo and the residue extracted with dichloromethane. The organic layer was dried over magnesium sulphate, filtered, concentrated in vacuo and the residue purified by flash chromatography (SiO$_2$, CH$_2$Cl$_2$/MeOH/NH$_4$OH 85/15/1) to afford 3-(7-aza-1H-indol-3-ylmethyl)-1-benzyl-piperazine (0.3 g); MH$^+$ 307, R$_f$ 0.51 (CH$_2$Cl$_2$/MeOH/NH$_4$OH 85/15/1).

The following compound was obtained according to a similar manner:

1-benzyl-3-(1H-indol-2-ylmethyl)piperazine); MH$^+$ 306, R$_f$ 0.32 (CH$_2$Cl$_2$/MeOH/NH$_4$OH 93/7/0.5).

What is claimed is:

1. A compound of the general formula (1)

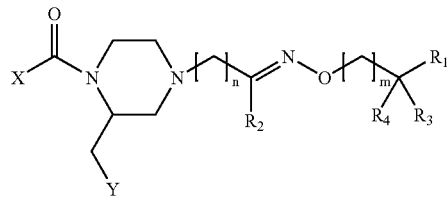
(1)

wherein:
X represents phenyl or pyridyl substituted with 1 or 2 substituents from the group $CH_3$, $CF_3$, $OCH_3$, halogen, cyano and 5-$CF_3$-tetrazol-1-yl;
Y represents 2- or 3-indolyl, phenyl, 7-aza-indol-3-yl or 3-indazolyl, 2-naphthyl, 3-benzo[b]thiophenyl or 2-benzofuranyl, which groups may be substituted with one or more halogen or alkyl (1–3C);
n has a value ranging from 0 to 3;
m has a value ranging from 0 to 2;
$R_1$ represents $NH_2$, NH-alkyl (1–3C), dialkyl (1–3C)N, morpholino or morpholino substituted with one or two methyl and/or methoxymethyl groups, thiomorpholino, 1,1-dioxothiomorpholino, 2-, 3- or 4-pyridyl or 4-$CH_3$-piperazinyl;
$R_2$ is hydrogen, alkyl (1–4C) or phenyl, or $R_2$ together with $(CH_2)_m$ wherein m is 1, and the intermediate carbon, nitrogen and oxygen atoms forms an isoxazolyl or a 4,5-dihydroisoxazolyl group; and
$R_3$ and $R_4$ independently represent hydrogen or methyl, or $R_3$ and $R_4$ together are oxygen;
or a physiologically acceptable salt thereof.

2. A compound as claimed in claim 1 having formula (1) wherein Y represents 2- or 3-indolyl, phenyl, 7-aza-indol-3-yl or 3-indazolyl, which groups may be substituted with one or more halogen or alkyl (1–3C); $R_1$ represents $NH_2$, NH-alkyl (1–3C), dialkyl (1–3C)N, morpholino or morpholino substituted with one or two methyl and/or methoxymethyl groups, thiomorpholino, 2-, 3- or 4-pyridyl or 4-$CH_3$-piperazinyl; $R_3$ and $R_4$ are independently hydrogen and X, n, m and $R_2$ have the meanings given in claim 1.

3. A compound as claimed in claim 1 having formula (1) wherein X represents phenyl substituted with 2 substituents from the group $CF_3$ and halogen, Y is 3-indolyl, m is 1 or 2, n is 1 or 2 and $R_1$, $R_2$, $R_3$, and $R_4$ have the meanings given in claim 1.

4. A compound as claimed in claim 3, wherein X represents phenyl substituted at positions 3 and 5 with $CF_3$ or halogen.

5. A method of preparing a compound of the general formula

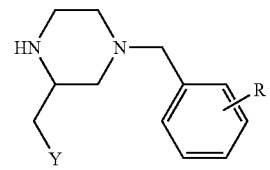

wherein R represents hydrogen, alkyl (1–4C) or O-alkyl (1–4C) and Y represents 2- or 3-indolyl, phenyl, 7-aza-indol-3-yl or 3-indazolyl, 2-naphthyl, 3-benzo[b]thiophenyl or 2-benzofuranyl, which groups may be substituted with one or more halogen or alkyl (1–3C);
wherein a solution of a compound of the general formula

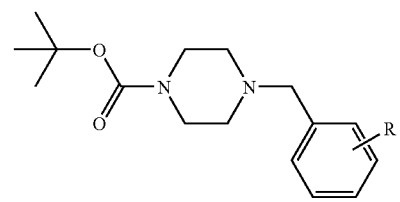

in the presence of a coordinating di- or triamine, is treated with a solution of an alkyl lithium base, followed by the addition of a compound of the general formula

Y—$CH_2$BR to yield a compound of the general formula

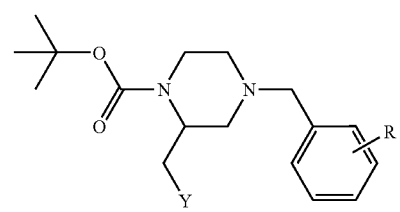

and removal of the tert-butyloxycarbonyl group.

6. A pharmaceutical composition containing a pharmacologically active amount of at least one compound of claim 1 as an active ingredient.

7. A method of preparing a pharmaceutical composition containing a pharmacologically active amount of at least one compound of claim 1 as an active inciredient, wherein said composition is brought into a form suitable for administration.

* * * * *